United States Patent [19]
Phan et al.

[11] Patent Number: 5,954,744
[45] Date of Patent: *Sep. 21, 1999

[54] INTRAVASCULAR STENT

[75] Inventors: Loc Phan, San Jose; Simon Stertzer, Woodside; Michael Froix, Mountian View, all of Calif.

[73] Assignee: Quanam Medical Corporation, Santa Clara, Calif.

[ * ] Notice: This patent is subject to a terminal disclaimer.

[21] Appl. No.: 08/884,106

[22] Filed: Jun. 26, 1997

Related U.S. Application Data

[63] Continuation-in-part of application No. 08/751,999, Nov. 15, 1996, Pat. No. 5,674,242, which is a continuation-in-part of application No. 08/486,271, Jun. 6, 1995, Pat. No. 5,603,722.

[51] Int. Cl.$^6$ .................................................. A61M 29/00
[52] U.S. Cl. ................................................. 606/198; 623/1
[58] Field of Search ................................... 606/198, 195, 606/192, 194; 623/1, 12

[56] References Cited

U.S. PATENT DOCUMENTS

| | | |
|---|---|---|
| 4,739,762 | 4/1988 | Palmaz . |
| 5,133,732 | 7/1992 | Wiktor . |
| 5,139,480 | 8/1992 | Hickle et al. . |
| 5,163,952 | 11/1992 | Froix . |
| 5,189,110 | 2/1993 | Ikematu et al. . |
| 5,195,984 | 3/1993 | Schatz . |
| 5,213,580 | 5/1993 | Slepian et al. . |
| 5,236,447 | 8/1993 | Kubo et al. . |
| 5,342,348 | 8/1994 | Kaplan . |
| 5,354,309 | 10/1994 | Schnepp-Pesch et al. . |
| 5,370,683 | 12/1994 | Fontaine . |
| 5,395,390 | 3/1995 | Simon et al. . |
| 5,603,722 | 2/1997 | Phan et al. . |
| 5,733,328 | 3/1998 | Fordenbacher ........................ 606/198 |

*Primary Examiner*—Michael Buiz
*Assistant Examiner*—Kevin Truong
*Attorney, Agent, or Firm*—Judy M. Mohr; Peter J. Dehlinger; Dehlinger & Associates

[57] ABSTRACT

A stent designed to be carried on the balloon of a balloon catheter to a target site is described. The stent is formed of a series of expandable, strip-like segments, each formed of a memory polymer and adapted for movement between a closed, high-curvature condition and an expanded, low-curvature condition upon exposure to a selected stimulus.

30 Claims, 4 Drawing Sheets

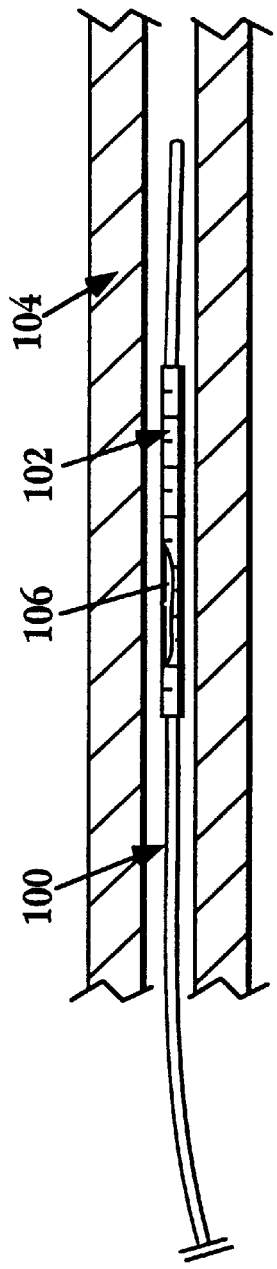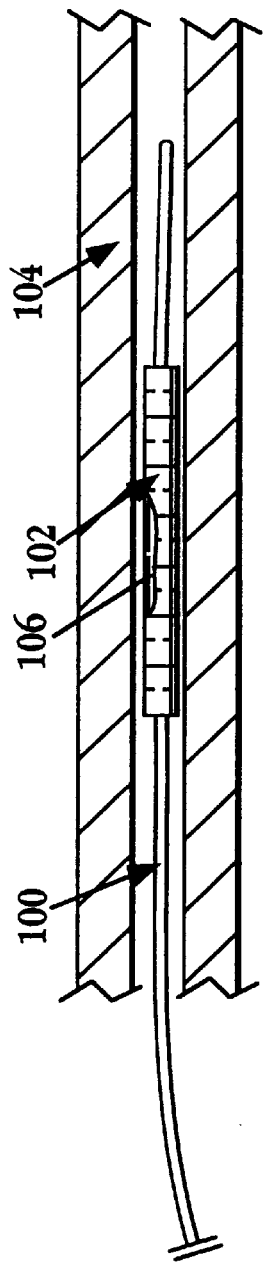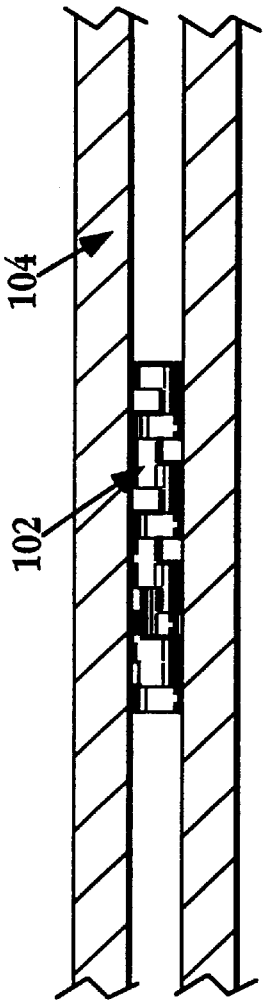

INTRAVASCULAR STENT

This application is a continuation-in-part application of co-pending U.S. patent application Ser. No. 08/751,999, filed Nov. 15, 1996 now U.S. Pat. No. 5,674,242, which is a continuation-in-part of U.S. Ser. No. 08/486,271 now U.S. Pat. No. 5,603,722 for "Intravascular Stent", filed Jun. 6, 1995, each of which is herein incorporated by reference.

FIELD OF THE INVENTION

The present invention relates to a stent which is formed of a memory polymer and designed to be carried on a balloon catheter to a target site in a vessel.

BACKGROUND OF THE INVENTION

Percutaneous transluminal angioplasty is one therapy used for selected atherosclerotic lesions to relieve stenosis of body lumens. While angioplasty has gained wide acceptance, abrupt closure and restenosis often occur following the procedure.

Endovascular stents have been used to mechanically block abrupt closure and restenosis of the lumen. Such stents are commonly made of metal or plastic and a variety of stents have been proposed and patented. Radially expandable stents formed of shape-memory alloys (Schnepp-Pesch, U.S. Pat. No. 5,354,309) and of polymers (Hickle, U.S. Pat. No. 5,139,480; Palmaz, U.S. Pat. No. 4,739,762), including shape-memory polymers (Froix, U.S. Pat. No. 5,163,952) have been described. One limitation of some of these stents is the axial expansion that occurs with the radial expansion. Axial expansion can make it difficult to size and correctly place the stent at the target site. Some stents are also often limited in expansion ratio, capable of expanding radially only two or four-fold.

SUMMARY OF THE INVENTION

In one aspect, the invention includes a stent designed to be carried on the balloon of a balloon catheter to a target site in a vessel. The stent includes a series of flexible, strip-like segments, each adapted for movement, in a substantially radial direction, between a closed, high-curvature condition and an expanded, low-curvature condition, upon exposure to a selected stimulus. The segments, so joined along offset side regions, that when coiled about a longitudinal axis form a cylindrical sleeve, and upon exposure to the stimulus, the segments in the stent expand toward their low-curvature condition until such movement is constrained by the walls of such vessel.

In one embodiment, the stent segments are joined to form a linear unitary strip, and in another embodiment, the stent segments are joined to form a V-shaped unitary strip.

Preferably, the strip segments are formed of a memory polymer, such as a methacrylate-containing polymer or an acrylate-containing polymer. The memory polymer may also be biodegradable or may contain a therapeutic agent for controlled release of the agent to the target site.

In general, the memory polymer may be a thermoplastic polymer, a crosslinked thermoplastic polymer, a thermoplastic polymer blend, or a crosslinked thermoplastic polymer blend.

The memory polymer forming the segments has a polymer-state transition that is activated by a stimulus, such as (a) adsorption of heat by the polymer; (b) adsorption of liquid by the polymer; or (c) a change in pH in a liquid in contact with the polymer.

In a preferred embodiment, the memory polymer has a thermally-activated polymer-state transition, where the transition involves (a) a melting point of the polymer; (b) a glass-transition of the polymer; (c) a liquid crystal transition; or (d) a local mode molecular transition. In a more preferred embodiment, the transition is a glass transition or a crystalline melting point at temperatures between about 25 and 65° C.

The stent segments in their open, low-curvature condition have an outer diameter of between about 0.1 mm to 5.0 cm, more preferably between 0.5 mm and 2.0 cm. Upon exposure to a stimulus, the segments expand from their closed, high-curvature condition toward their expanded, low-curvature condition. The expansion ratio of the stent, that is the ratio of the stent's outer diameter in the expanded, open condition to the closed condition is between about 2–10 for small target vessels and up to 500–2,000 for larger target vessels.

In another aspect, the invention includes a balloon-catheter apparatus for delivering a stent to a target site in a vessel. The apparatus includes a balloon catheter having at one end a balloon that can be filled with a liquid. Carried on the balloon of the catheter, is a stent, as described above in accordance with the present invention.

These and other objects and features of the invention will be more fully appreciated when the following detailed description of the invention is read in conjunction with the accompanying drawings.

BRIEF DESCRIPTION OF THE DRAWINGS

FIGS. 4A–4C show a method of positioning the stent in a blood vessel, where the stent is fitted snugly around a balloon catheter (FIG. 4A), the stent is raised to its transition temperature for expansion toward its memory condition (FIG. 4B) and the catheter is withdrawn, leaving the stent in its expanded condition pressing against the sides of the target vessel (FIG. 4C).

DETAILED DESCRIPTION OF THE INVENTION

The stent of the present invention is designed to be carried on the balloon of a balloon catheter to a target site in a vessel. In particular, the stent is intended for use in a vessel to prevent post-angioplasty vessel reclosure, or restenosis. In general, the stent is suitable for use in a variety of body cavities, such as artery, bile duct, ureter, fallopian tube or tear duct, for a variety of purposes.

Figure 1A:
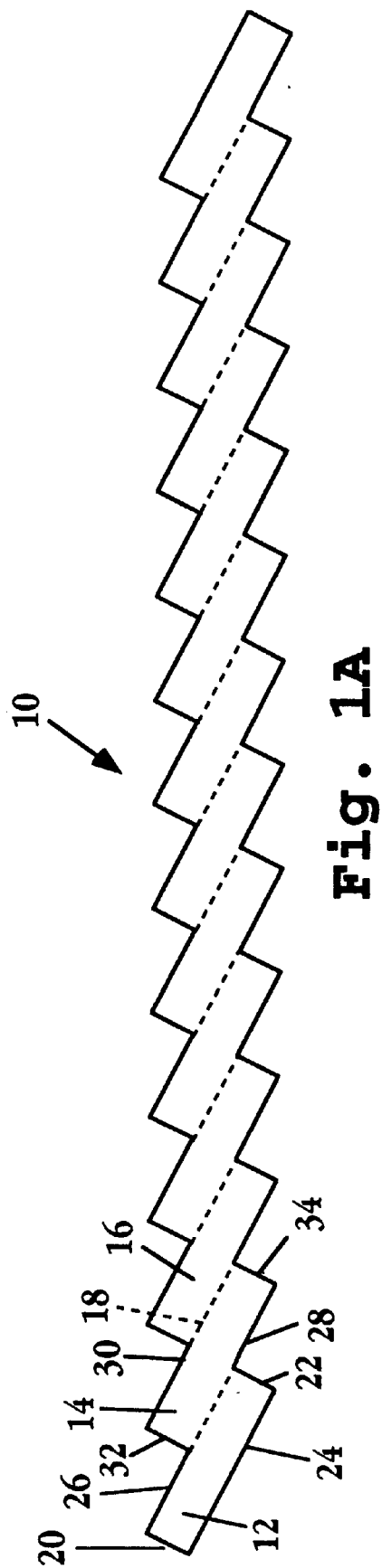
FIGS. 1A–1C show one embodiment of the stent of the present invention, where the stent is in its memory condition (FIG. 1A), in its closed, high-curvature condition (FIG. 1B) and in its expanded, low-curvature condition (FIG. 1C)
Figure 1B:
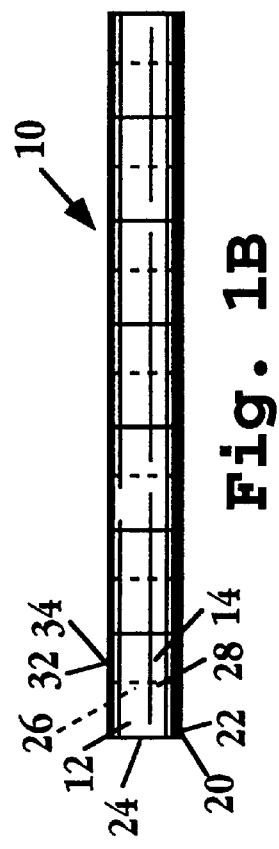
Figure 1C:
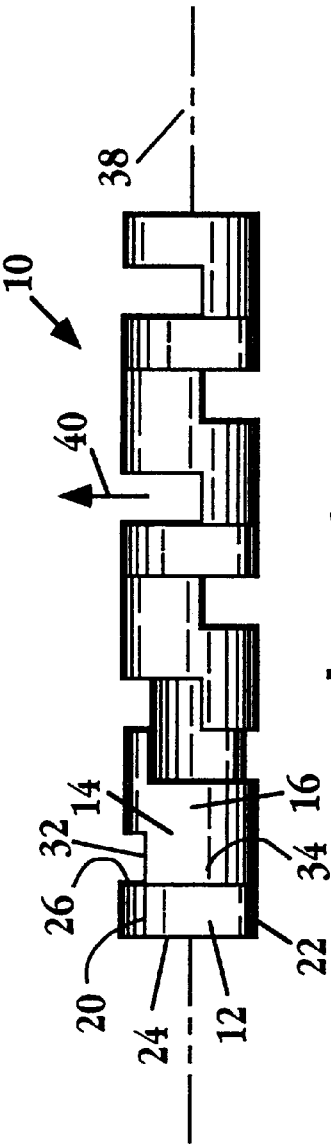

As seen in FIGS. 1A–1C, the stent is formed of a series of flexible strip-like segments, as seen best in FIG. 1A. Stent 10, is a linear, unitary strip formed of a series of segments, such as segments 12, 14, 16. The dashed lines in the figure, such as line 18, are drawn to aid in visualizing the strip segments. Segment 12, which is representative, is defined by ends 20, 22 and sides 24, 26.

The segments are joined along offsetting side regions, that is, the segments, when placed in a side-to-side or top-to-bottom direction, are positioned such that the upper side (or end) of one segment joins the lower side (or end) of an adjacent segment, and the upper side (or end) of the adjacent segment joins the lower side (or end) of a further adjacent segment, and so on. For example, in FIG. 1A, segments 12 and 14 are joined along sides 26 and 28, where side 26 is the upper side of segment 12 and side 28 is the lower side of segment 14. The segments are joined along common sides in this offset fashion, e.g., segments 12, 14 are joined along sides 26, 28, which are offset from one another.

The stent segments are formed of a memory polymer, which has a preselected memory condition, as will be described in more detail below. As shown in FIG. 1A, the memory condition of stent 10 is a flat strip, however, a memory condition of another geometry, such as a tubular shape, is also possible.

The memory polymer, described below, is formulated to have a polymer-state transition that responds to a selected stimulus. Upon exposure to the stimulus, the polymer transition is activated and the stent moves between its closed, high-curvature condition toward its memory condition. The polymer transition can be activated by adsorption of heat, adsorption of liquid, or a change in pH in a liquid in contact with the polymer. Preferably, the transition is activated by a thermal stimulus, where, at a preselected temperature, the polymer undergoes a transition, such as a crystalline melting point of the either the main chain or a side chain of the polymer, preferably between about 25–65° C. The thermal transition may also be a glass-transition at a temperature of between 25–65° C., a liquid-crystal phase (mesophase) temperature transition, or a local mode molecular transition.

Each strip segment is initially placed from its memory condition into a closed, high-curvature condition by exposing the polymer stent to one of the above mentioned stimuli. For example, the segments are heated to or just above their glass transition temperature, at which point the segments become more flexible and rubbery. The strip segments are each placed in their closed condition by forcing the segments into the small-diameter, high-curvature state, for example, by wrapping or winding the segments around a balloon region in a balloon catheter.

FIG. 1B shows stent 10 of FIG. 1A with the segments in their closed, high-curvature conditions. Segment 12 of FIG. 1A, which is representative, is brought to its closed condition by warming the polymer to or above its transition, and then bringing the segments ends 20, 22 together. A segment in its closed condition may have its ends in contact, as illustrated in FIG. 1B, or there may be a gap between the segment ends. The segments remain in their closed conditions when the polymer cools below the transition temperature, or the stimulus is removed.

As can be seen in FIG. 1B, when the strip segments are in their closed conditions, the stent takes the form of a flexible, small-diameter sleeve having a high radius of curvature. As will be described below, the stent in its closed condition fits snugly on an uninflated balloon of a balloon catheter for delivery to a target site in a vessel.

FIG. 1C shows stent 10 with each strip-like segment in an expanded, low-curvature condition. The segments move from their closed, high-curvature condition to their open, low-curvature condition upon exposure to a selected stimulus, as discussed above, such a adsorption of heat. For example, warm saline or other appropriate liquid in a temperature range of 25–100° C., more preferably 40–100° C., is injected into the balloon of the catheter. Heat is transferred from the liquid to the polymer stent, and at a selected temperature the polymer undergoes a thermal transition where the stent segments become flexible and begin to move toward their memory condition. The segments expand until movement is constrained by the walls of the vessel, placing the stent in its open, expanded-diameter, low-curvature condition.

As the stent segments expand from their high-curvature conditions toward their low-curvature conditions, movement occurs in a substantially radial direction. As illustrated in FIG. 1C, stent 10 has a longitudinal axis, indicated by dashed line 38. Upon exposure to a stimulus, the segments expand radially, that is normal to axis 38, as indicated by arrow 40. Upon expansion of the stent to its low-curvature, open condition, there is little axial lengthening of the stent. Thus, as the stent expands there is little or no lateral movement of the stent in the vessel. The stent is deployed easily and placed securely at the target site.

The size, diameter and length, of the stent is tailored to each specific application. For example, for cardiovascular applications, the stent can have a length ranging from 0.5 cm to approximately 3 cm. The diameter of the stent in its open condition can range from 0.1 mm to 5 cm, depending on the inner diameter of the target vessel. Small body vessels, such as a brain vessel, have an inner diameter of about 0.1 mm. Larger body vessels, such as the aorta, are around 3–5 cm in diameter, depending on the size of the individual. The expansion ratio of the stent, that is the ratio of the stent's outer diameter in the expanded, open condition to the closed condition is between about 2 and 2,000, depending on the polymer, amount of crosslinking, and other parameters.

According to an important feature of the invention, the stent is formed of a shape-memory polymer, in general from a thermoplastic polymer, and in particular from a methacrylate-containing or acrylate-containing polymers, as described in U.S. Pat. No. 5,163,952, which is incorporated by reference herein. Thermoplastic polymer as used herein refers to those polymers that can be made to soften and take on a new shape by the application of heat and/or pressure. Such polymers can be crosslinked to varying degrees so that the polymer will soften with heat but not flow. The memory polymer may also be a biodegradable polymer.

The polymer is characterized in that it will attempt to assume its memory condition by activation of a polymer transition. Activation can occur by adsorption of heat by the polymer, adsorption of liquid by the polymer, or a change in pH in the liquid in contact with the polymer. The polymer is formulated to be responsive to adsorption of a liquid by incorporating in the polymer a hydrophilic material, such a n-vinyl pyrrolidone. Incorporation of a material such as methacrylic acid or acrylic acid into the polymer results in a polymer having a transition that is sensitive to pH. The polymer transition may be a thermally activated transition, where upon adsorption of heat the polymer undergoes a glass transition or a crystalline melting point.

The stent segments expand from their closed, high-curvature condition towards its memory condition as the polymer responds to a stimulus and undergoes one of the above transitions. Similarly, the stent segments can be moved from their initial, memory conditions to their closed, high-curvature conditions, or from their open, low-curvature conditions to their closed conditions, as the polymer undergoes one of the transitions.

An exemplary methacrylate-containing memory polymer is prepared by mixing the monomers methyl methacrylate, polyethyleneglycol methacrylate, butylmethacrylate in a 2:1.5:1 ratio. A crosslinker, such as hexanedioldimethacrylate, and a thermal or UV initiator, such as benzoin methyl ether or azobisisobutylnitrile (AIBN), are added and the formulation is stirred as polymerization proceeds. The monomers can be polymerized into a polymer for extrusion in a conventional extruder to provide a length of a tubular structure or a flat sheet, which are crosslinked by exposure to UV light, high energy electrons, gamma radiation or heat. The monomers can also be polymerized in a transparent spinning tube to form a tubular structure.

Another exemplary thermoplastic polymer is polyethylene oxide, a heterochain thermoplastic with a crystalline melting point around 65° C. Polyethylene oxide can be crosslinked using a multifunctional acrylate or methacrylate, such as triallylisocyanurate. Thermoplastic blends are also suitable memory polymers, such as blends of polyethylene oxide with methylmethacrylate, polyethylene, polycaprolactone, or trans-polyoctenamer (Vestenamer®). Typically, between 30–70% of polyethylene oxide is present in the blends. The blends can be crosslinked using conventional multifunctional crosslinkers.

The polymer tube or flat sheet is then cut to suitable dimensions, typically, a length between about 0.5 cm and 3.0 cm. The stent's inner diameter can range from approximately 0.05 mm to 5 cm, with a wall thickness, or sheet thickness, of between 0.01 mm to 0.5 mm, preferably 0.05–0.5 mm.

It will be appreciated that the original shape, tubular or flat sheet, of the stent is the preselected memory condition of the stent segments. That is, when the polymer undergoes a selected transition, the polymer will recover toward its memory condition, as will be described in more detail below.

The extruded polymer tube or sheet is formed into a stent as described herein, that is an elongate strip having a series of expandable segment adapted for movement by cutting, such as laser cutting, or other methods. The stent segments are placed from their memory conditions to their closed conditions by, for example, heating the segments to or above their thermal transition temperature, forcing the strip segments into their closed conditions, and cooling the segments below the transition temperature. Typically, the stent segments are wound around the balloon of a balloon-type catheter, for placement at a target site, as will be described.

In one embodiment of the invention, the stent includes a therapeutic agent for controlled release of the agent at the target site. The agent can be incorporated into the stent by passive diffusion after fabrication of the stent, or more preferably, by addition of the agent prior to extruding the polymer or prior to polymerization of the polymer sheet or tube. Exemplary therapeutic agents include heparin to prevent thrombus formation; an antiproliferative agent, such as methotrexate; a vasodilator, such as a calcium channel blocker; a nitrate; antiplatelet agents, such as ticlopidine or abciximab (ReoPro™); or clot dissolving enzymes, such as tissue plasminogen activator. Another agent may be finasteride (Proscar®) for treatment of benign prostatic hyperplasia.

In another embodiment of the invention, the stent includes a radio-opaque material, such as gold, stainless steel, platinum, tantalum, metal salts, such as barium sulfate, or iodine containing agents, such as OmniPaque® (Sanofi Winthrop Pharmaceuticals). The radio-opaque material may be incorporated into the memory polymer prior to the extrusion of stent, or a radio-opaque coating may be applied to the stent. The radio-opaque material provides a means for identifying the location of the stent by x-rays or other imaging techniques during or after stent placement.

Figure 2A:
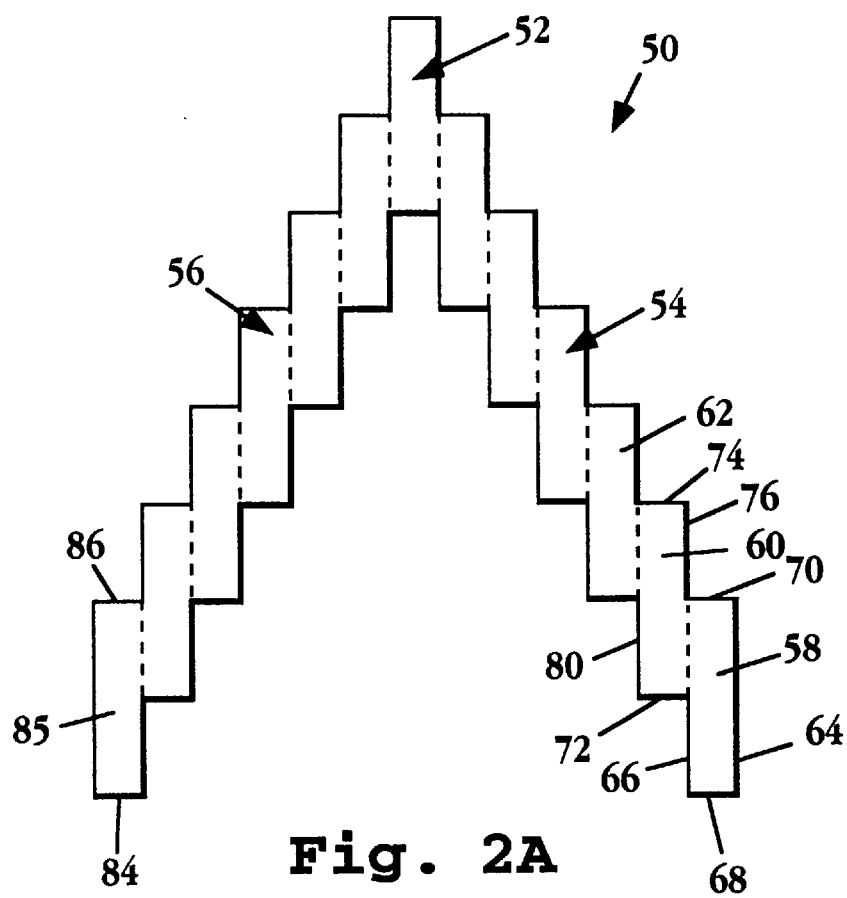
FIGS. 2A–2C show another embodiment of the stent where the stent segments are joined to form a V-shaped strip, and where the stent is in its memory condition (FIG. 2A), in its closed condition (FIG. 2B) and in its expanded condition (FIG. 2C)
Figure 2B:
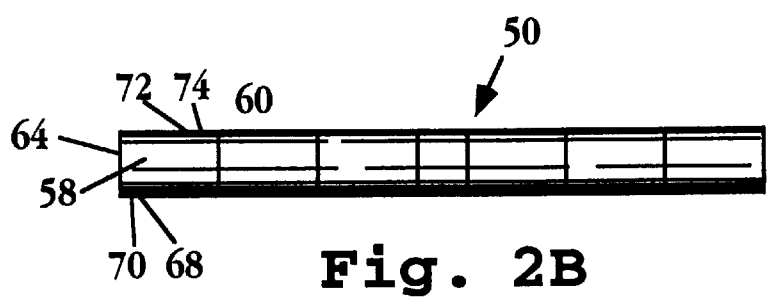
Figure 2C:
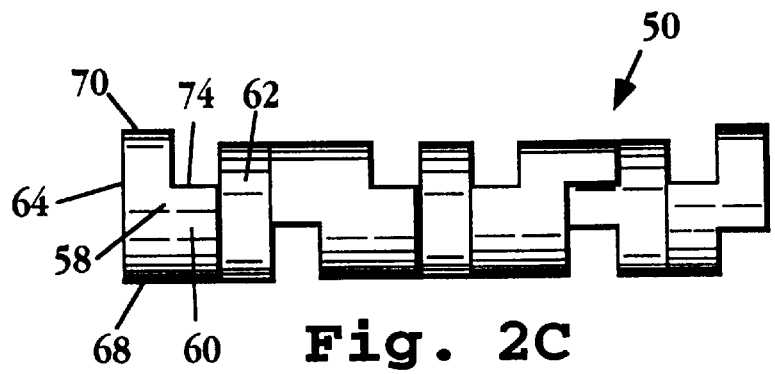

FIGS. 2A–2C show a second embodiment of the stent of the present invention, where stent 50 is formed of a series of expandable, strip-like segments joined to form a v-shaped unitary strip. As seen in FIG. 2A, the v-shaped unitary strip 52 has two portions or legs 54, 56, each formed of a plurality of segments, such as segments 58, 60, 62. Segment 58, which is representative, is defined by sides 64, 66 and ends 68, 70.

The strip-like segments are joined along common, offset side regions. Segments 58, 60 are joined along offset sides 66, of segment 64, and 76, of segment 60. Strip 52 is shown in FIG. 2A in its memory condition as a flat strip, but it will be appreciated that strip 52 may also take the form of a tubular structure as its preselected memory condition.

Each strip segment is placed in its closed, high-curvature condition, as shown in FIG. 2B, by exposing the strip segments to a stimulus, as discussed above, to activate a polymer transition. For example, the polymer segments can be heated to their glass transition temperature or to their crystalline melting point. The heated strip segments are wound around a balloon catheter and cooled below the transition temperature to secure the segments in their closed conditions.

FIG. 2B shows the strip of FIG. 2A with the segments in their closed, high-curvature conditions to form a flexible, cylindrical sleeve. The ends of each strip segment, such as ends 68, 70 of segment 58 are brought together, to place that segment in its closed condition. The ends of each segment in its closed condition may be touching or there may be a space between the ends.

Strip 52 can be wound into its closed condition by wrapping legs 54, 56 in the same directions or in opposite directions. For example, leg 54 can be wrapped in a first direction, where end 68 is brought under segment 58 to contact end 70. Leg 56 is wound in the opposite direction, by bring end 84 over segment 85 to contact end 86.

As can be seen in FIGS. 1B and 2B, the ends of each segment in the stent, when the stent is in its closed condition being coiled into a cylindrical sleeve, are distributed around the perimeter of the stent. This results in a uniform distribution of force around the perimeter of the stent, which is advantageous during insertion of the stent as the stent will have less tendency to buckle or snag while being placed in a vessel. The distribution of forces around the perimeter of the stent is also advantageous with the stent in its expanded condition, allowing the stent to more stably and securely open a constricted vessel.

With continuing reference to FIGS. 2A–2B, upon exposure to a stimulus, the segments of each leg expand radially but in opposite directions. The stent expands in the vessel with little or no lateral movement, thereby allowing easy, precise placement of the stent at the target site in the vessel.

FIG. 2C shows the stent with the strip segments expanded, by radial movement, into their open, low-curvature conditions. The segments are expanded by exposing the stent to a stimuli, such as heat, to activate a polymer-state transition, such as a glass transition. The segments expand radially towards their memory condition, until movement of the segments is constrained by the walls of the vessel. In this way, the stent is placed in the vessel in its expanded, low-curvature condition.

The invention also contemplates a stent formed of a v-shaped elongate polymer strip. In this embodiment, the strip is shaped similar to that shown in FIG. 2A, that is a v-shape with two leg portions. Each leg portion is formed of a single strip segment which is helically wound to place the strip in its closed, high-curvature condition. As described above, the legs of the strip are wound in opposite directions, so that upon expansion to the open, low-curvature condition, the legs unwind in opposite directions.

Figure 3A:
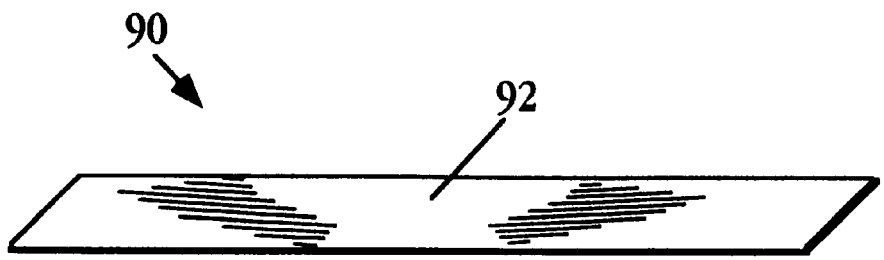
FIGS. 3A–3C show a stent formed of an elongate strip having a single parallelogram-shaped segment, where the stent is in its memory condition (FIG. 3A), in its a closed condition (FIG. 3B) and in its expanded condition (FIG. 3C)
Figure 3B:
Figure 3C:

FIGS. 3A–3C shows a stent 90 formed of an elongate strip having one strip segment, where the segment has the shape of a parallelogram (FIGS. 3A–3C). As seen in FIG. 3A, segment 92 in its memory condition is a flat strip having the shape of a parallelogram. The segment is placed into its closed, high-curvature condition by activating the polymer transition and winding the segment around a balloon catheter. The segment is cooled below its transition to secure the segment in its high-curvature, small-diameter configuration, as illustrated in FIG. 3B. In this configuration, the stent takes the form of a flexible, cylindrical sleeve. The segment, upon activation of the polymer transition, expands toward its memory condition, to its open, low-curvature condition, as shown in FIG. 3C. Expansion continues until the vessel walls constrain such movement.

As discussed above, the stent of the present invention, when used for prevention of restenosis of arteries, will generally be placed by transluminal angioplasty catheters. As seen in FIG. 4A, a balloon catheter 100 is used to deliver the stent 102 to a region of stenosis in a blood vessel 104. Stent 102 takes the form of a flexible, cylindrical sleeve that is carried, with each stent segment in its closed, low-curvature condition, on the uninflated balloon 106 of catheter 100. The catheter is introduced over a conventional guidewire and the stent is positioned within the target site using, for example, fluoroscopic imaging.

Once the stent is properly positioned, balloon 106 is filled with a liquid to stimulate the polymer-state transition of the stent. As discussed above, the polymer transition may be thermally induced or may be activated by a change in pH or adsorption of a liquid. Upon exposure to the stimulus, the stent expands from its closed, small-diameter condition toward its memory condition. For example, a stent having a thermally activated polymer transition is stimulated to expand by filling the catheter balloon with a heated liquid, such as a contrast agent heated to between about 40–100° C. Heat from the liquid is adsorbed by the polymer stent. The catheter itself may be specifically designed for injection of a heated liquid and for better heat transfer. For example, the catheter may have a double lumen for recirculation of the heated liquid in the balloon region of the catheter.

The stimulus may also be a pH stimulus or a liquid stimulus, where a buffer solution of a selected pH is introduced into the balloon. Small openings in the balloon, introduced prior to placement of the stent around the balloon, would allow the liquid to contact the stent. The term "upon exposure to the liquid" as used herein is meant to include exposure of the stent to the heat of a heated liquid and exposure to the liquid itself.

In a preferred embodiment, the stimulus is a thermal stimulus, and a heated liquid is introduced into the balloon. Heat from the liquid is conducted convectively to the polymer stent, raising the temperature of the stent to its thermal transition, such as a glass transition temperature of between about 25–60° C., more preferably between 30–50° C., and most preferably between 35–48° C. As illustrated in FIG. 4B, the stent segments respond to the stimulus by moving toward their memory condition. As can be seen, stent 102 expands radially towards its expanded, low-curvature condition. Movement continues until the segments are constrained by the vessel walls, as illustrated in FIG. 4C. Once the stent is fully deployed with the segments in their low-curvature, expanded condition, the catheter may be withdrawn over the guidewire, and the guidewire removed.

Although the invention has been described with respect to particular embodiments, it will be apparent to those skilled in the art that various changes and modifications can be made without departing from the invention.

It is claimed:

1. A stent designed to be carried on the balloon of a balloon catheter to a target site in a vessel, comprising a series of flexible, strip-like segments, each adapted for movement, in a substantially radial direction, between a closed, high-curvature condition and an expanded, low-curvature condition, upon exposure to a selected stimulus, said segments being so joined along offset side regions that they form initially a step-like strip which when helically wound about a longitudinal axis form a cylindrical sleeve, and upon exposure to said stimulus, the segments in the stent expand toward their low-curvature condition until such movement is constrained by the walls of such vessel.

2. The stent of claim 1, wherein said segments are joined to form a linear unitary strip.

3. The stent of claim 1, wherein said segments are joined to form a V-shaped unitary strip.

4. The stent of claim 1, wherein said strip segments are formed of a memory polymer.

5. The stent of claim 4, wherein said strip segments are formed of a thermoplastic polymer.

6. The stent of claim 4, wherein said strip segments are formed of a crosslinked thermoplastic polymer.

7. The stent of claim 4, wherein said strip segments are formed of a thermoplastic polymer blend.

8. The stent of claim 4, wherein said strip segments are formed of a crosslinked thermoplastic polymer blend.

9. The stent of claim 4, wherein said memory polymer is a methacrylate-containing polymer.

10. The stent of claim 4, wherein said memory polymer is an acrylate-containing polymer.

11. The stent of claim 4, wherein said memory polymer is biodegradable.

12. The stent of claim 4, wherein said segments contain a therapeutic agent for controlled release of said agent to the target site.

13. The stent of claim 1, wherein said segments are formed of a memory polymer having a polymer-state transition that is activated by one of the following stimuli:

(a) adsorption of heat by said polymer;

(b) adsorption of liquid by said polymer; and (c) a change in pH in a liquid in contact with said polymer.

14. The stent of claim 1, wherein said segments are formed of a memory polymer having a thermally-activated polymer-state transition selected from the group consisting of:

(a) a melting point of the polymer;

(b) a glass-transition of the polymer;

(c) a liquid crystal transition; and (d) a local mode molecular transition.

15. The stent of claim 14, wherein said transition is a glass transition between about 25 and 65° C.

16. The stent of claim 14, wherein said transition is a crystalline melting point between about 25 and 65° C.

17. The stent of claim 1, wherein said segments in their open, low-curvature condition have an outer diameter of between about 0.1 mm to 5 cm.

18. The stent of claim 1, wherein said segments have an expansion ratio of between about 2–2,000.

19. A balloon-catheter apparatus for delivering a stent to a target site in a vessel, comprising a balloon catheter having at one end a balloon that can be filled with a liquid;

a stent, formed of a series of flexible, strip-like segments, each adapted for movement, in a substantially radial direction, between a closed, high-curvature condition and an expanded, low-curvature condition, upon exposure to said liquid;

said segments so joined along offset side regions that when coiled about a longitudinal axis form a cylindrical sleeve, and upon exposure to said liquid, the segments in the stent expand toward their low-curvature condition until such movement is constrained by the walls of such vessel.

20. The apparatus of claim 19, wherein said stent is formed of a memory polymer having a polymer-state transition that is activated by one of the following:

(a) adsorption of heat by said polymer;

(b) adsorption of liquid by said polymer; and (c) a change in pH in a liquid in contact with said polymer.

21. The apparatus of claim 20, wherein said liquid is heated to a temperature of between 25–100° C., and said transition is a thermal transition, activated by adsorption of heat from said liquid, selected from one of the following:

(a) a melting point of the polymer;

(b) a glass-transition of the polymer;

(c) a liquid crystal transition; and (d) a local mode molecular transition.

22. The stent of claim 20, wherein said transition is a glass transition between about 25 and 65° C.

23. The stent of claim 20, wherein said memory polymer is a methacrylate-containing polymer.

24. The stent of claim 20, wherein said memory polymer is an acrylate-containing polymer.

25. The stent of claim 20, wherein said memory polymer is biodegradable.

26. The stent of claim 20, wherein said strip segments are formed of a thermoplastic polymer.

27. The stent of claim 20, wherein said strip segments are formed of a crosslinked thermoplastic polymer.

28. The stent of claim 20, wherein said strip segments are formed of a thermoplastic polymer blend.

29. The stent of claim 20, wherein said strip segments are formed of a crosslinked thermoplastic polymer blend.

30. The stent of claim 20, wherein said segments contain a therapeutic agent for controlled release of said agent to the target site.

* * * * *